United States Patent [19]

Hanstein et al.

[11] Patent Number: 4,885,281

[45] Date of Patent: Dec. 5, 1989

[54] SUCRALFATE SUSPENSION

[75] Inventors: Ullrich Hanstein, Mühltal; Lothar Bauer, Pfungstadst, both of Fed. Rep. of Germany

[73] Assignee: Merck Patent Gesellschaft mit beschränkter Haftung, Darmstadt, Fed. Rep. of Germany

[21] Appl. No.: 171,347

[22] Filed: Mar. 21, 1988

Related U.S. Application Data

[63] Continuation-in-part of Ser. No. 878,869, Apr. 22, 1986, abandoned.

[30] Foreign Application Priority Data

Aug. 22, 1984 [DE] Fed. Rep. of Germany ....... 3430807

[51] Int. Cl.$^4$ ............................................. A61K 31/70
[52] U.S. Cl. ......................................... 514/53; 514/54
[58] Field of Search ............................. 514/54, 23, 53

[56] References Cited

FOREIGN PATENT DOCUMENTS 0055313 7/1982 European Pat. Off. .
0107209 2/1984 European Pat. Off. .

*Primary Examiner*—Amelia Burgess Yarbrough
*Assistant Examiner*—Elli Peselev
*Attorney, Agent, or Firm*—Millen, White & Zelano

[57] ABSTRACT

The invention relates to formulations in the form of suspensions containing sucralfate, characterized in that they contain, based on the sucralfate, 1–5% by weight of xanthan gum and 1–12.5% by weight of at least one peptiser.

4 Claims, No Drawings

SUCRALFATE SUSPENSION

This application is a continuation in part of application Ser. No. 878,869 filed Apr. 22, 1986, now abandoned.

The invention relates to pharmaceutical formulations in the form of suspensions containing sucralfate as the pharmaceutical active compound.

Sucralfate (Ulcogant(®)) is a basic aluminium sucrose sulfate. It is known from German Offenlegungsschrift 1,568,346 and is used in human medicine for relieving the symptoms of gastric and duodenal ulcers and for accelerating the healing of ulcers. An advantageous action of sucralfate in combating emesis and/or diarrhoea in veterinary medicine has moreover been described in German Patent Application P 3,322,078.

The action of sucralfate is characterised by pepsinbinding and antacid effects. Sucralfate, which is tolerated very well, displays its action in the acid medium of the digestive tract, in particular at pH values below 4, where it lines the mucous membranes of the stomach and duodenum with a protective coating. As a result of its preferential binding affinity for areas of the mucous membrane which have been attacked, increased protection and accelerated healing of ulcers as well as regeneration of the mucous membrane and its functions occur there.

Formulations containing sucralfate have hitherto usually been employed only in the form of solid administration forms, such as tablets, granules or powders. However, liquid formulations, for example in the form of suspensions, would be advantageous for the particular mode of action of sucralfate, especially in view of a rapid and complete lining of the mucous membranes in the digestive tract. It is indeed possible to suspend the commercially available solid administration forms, for example in water, before use and to take them in this form. However, this proves to be inconvenient and is frequently found to be unpleasant in taste for the patient taking the medicament, and is thus not very practicable. Attempts to prepare sucralfate-containing finished medicaments in the form of suspensions have hitherto failed, since no suspensions which are stable for a prolonged period could be obtained with the customary auxiliaries. In such suspensions, the solid sedimented out after a short time and formed lumps to such an extent that in some cases it could not be shaken up again.

The invention was thus based on the object of discovering a method of stabilising pharmaceutical formulations in the form of suspensions containing sucralfate, and a corresponding stable formulation as the finished medicament.

For the formulation of pharmaceutical suspensions, attempts are made to prevent sedimentation of the suspended particles, or at least to keep the sedimentation as low as possible, by suitable additives. This is to ensure that the agent remains homogeneous and can be used appropriately even after prolonged storage. If sedimentation nevertheless takes place in the course of time, it should be ensured that the solid can readily be shaken up. Moreover, suspensions for oral use should be given, as far as possible, a pleasant or at least neutral taste. In particular, the solid content should be incorporated such that this or the solid particles are not found to be troublesome when the suspension is taken. In the case of aqueous suspensions, the properties mentioned can usually be achieved by adding liquids which increase the viscosity, such as glycerol, propanediol, sorbitol solution and/or liquid polyethylene glycols, and by incorporating suspending agents and thickeners. Agents of this type which increase the viscosity and prevent sedimentation of the solid particles are usually high molecular weight cellulose derivatives or polysaccharide gums, such as, for example, carboxymethylcelluloses, methylcelluloses, alginates or tragacanth.

Numerous attempts have been made, with only little or no success, to achieve the object of developing a stable sucralfate suspension which does not sediment. For this, the essential familiar suspending agents and thickeners customary in the technology of pharmaceutical suspensions and corresponding auxiliaries and additives were tested. It was found that, evidently due to the property of the sucralfate of releasing $Al^{3+}$ ions in an aqueous medium, interactions are induced with virtually all the thickening substances, and these sometimes lead to drastic decreases or increases in viscosity and to precipitation of the thickeners. This means that the sucralfate particles in such suspension formulations sediment very rapidly, forming lumpy precipitates which deposit and stick to the walls of the packaging material and can no longer be shaken up.

It has been found that, surprisingly, stable formulations can be obtained in the form of suspensions containing sucralfate if 1-5% by weight of xanthan gum and 1-12.5% by weight of at least one peptiser, based on the content of sucralfate, are added to these formulations.

The invention accordingly relates to pharmaceutical formulations in the form of suspensions containing sucralfate, which have a content, based on the sucralfate, of 1-5% by weight of xanthan gum and 1-12.5% by weight of at least one peptiser.

The invention particularly relates to such a pharmaceutical formulation in which the peptiser is at least one salt of phosphoric acid and/or citric acid.

The invention moreover relates to a method of stabilising pharmaceutical formulations in the form of suspensions containing sucralfate, 1-5% by weight of xanthan gum and 1-12.5% by weight of at least one peptiser, based on the content of sucralfate, being added to these formulations.

Xanthan gum ("Polysaccharide 1459") is a high molecular weight polysaccharide which can be obtained by fermentation of carbohydrates with Pseudomonas microbes, especially with Xanthomonas campestris, and is usually in the form of its alkali metal and/or alkaline earth metal salts. It is known that xanthan gum, inter alia, can also be used as a suspending agent and thickener for pharmaceutical and cosmetic products (see H. P. Fiedler, Lexikon der Hilfsstoffe (Lexicon of Auxiliaries), page 1016, 2nd edition (1981) or The United States Pharmacopeia, Twentieth Revision (1980)). Thus a basic aluminium salt of xanthan gum is known as a pharmaceutical excipient, as well as the use thereof as a suspending agent for barium sulfate in radiographic contrast media (compare Chemical Abstracts 79 (1973) 23582m and 81 (1973) 96461x). On the other hand, however, work is also known in which xanthan gum is used for flocculating metal oxides, hydroxides, carbonates, in particular also of aluminium, from suspensions (Chemical Abstracts 94 (1981) 52786w, 95 (1981) 12692b and 96 (1982) 24726z). From the prior art, it could thus not be assumed that xanthan gum is generally suitable for stabilising pharmaceutical suspensions containing sucralfate. Rather, it was found in the numerous experiments carried out that a satisfactory solution of the problem was hardly to be seen in xanthan gum, as in all the other usual thickeners, even in combination with other auxiliaries and additives customary in the technology of pharmaceutical suspensions.

The result that a combination of the medicinal substance sucralfate, the thickener xanthan gum and at least one peptiser leads to a stable sucralfate suspension which fulfils the requirements of galenics and of medicinal use in an outstanding manner if the amounts in the composition are chosen according to the invention was all the more surprising.

The sucralfate used for the preparation of the sucralfate suspensions according to the invention is a familiar pharmaceutical active compound and is used here preferably in the finely ground form with a particle size of below 50 μm.

The xanthan gum used, according to the invention, as the suspending agent and thickener can be prepared on an industrial scale by fermentation processes and is commercially available in accordance with the quality specifications of the pharmacopoeias of various countries.

The peptisers to be added, according to the invention, to the suspension are salts of inorganic or organic acids, which are intended to ensure that the high molecular weight additive xanthan gum remains in the sol state, that is to say in homogeneous distribution, in disperse systems such as the present suspensions, and does not separate out by gel formation. These peptisers can be, for example, physiologically acceptable salts of phosphoric acid, citric acid or other tribasic acids. Salts of phosphoric acid and citric acid are particularly suitable here. Sodium dihydrogen phosphate is particularly preferred.

According to the invention, 1–5% by weight of xanthan gum and 1–12.5% by weight of at least one peptiser, based on the content of sucralfate, are added to the sucralfate suspensions for effective, permanent stabilisation. The content of sucralfate in these formulations can vary within wide limits.

As a rule, such suspensions can contain 1–40% by weight of sucralfate, based on the total amount. Typical formulations of sucralfate suspensions according to the invention contain, based on the total amount, 1–40% by weight, preferably 10–25% by weight, of sucralfate, 0.01–2% by weight, preferably 0.1–1% by weight, of xanthan gum and 0.01–5% by weight, preferably 0.1–3% by weight, of peptiser. Besides water as the liquid medium, the suspensions according to the invention can also contain liquids which increase the viscosity, preferably glycerol or propanediol, in an amount of 1–50% by weight, preferably 10–20% by weight. Moreover, the addition of other auxiliaries and additives customary in the technology of pharmaceutical suspensions is possible. These chiefly include preservatives, such as, for example, sodium methyl-4-hydroxybenzoate and sodium propyl-4-hydroxybenzoate, which are added together or individually in the usual concentrations of, for example, about 0.1% by weight. Flavour-improving aromas, sweeteners and flavour correctants can also be added. Additives of this type as a rule scarcely exceed a content of 1% by weight, based on the total amount. Other active compounds can also be added to the sucralfate suspensions according to the invention, for example those with which it is known that sucralfate can be combined, such as, for example, antacids, spasmolytics, antiflatulents, $H_2$-receptor blockers, non-steroid antirheumatics and generally acid secretion-inhibiting drugs. These also include those aminoacids described in European Patent A1-0,107,209 which intensify the effect of sucralfate in lining the mucous membrane or which are to retain this effect in the case of adverse storage conditions of corresponding products.

The sucralfate suspensions according to the invention are prepared in a manner which is known per se, by mixing the components and homogenising. They can then be filled into the customary means of packaging for pharmaceutical suspensions, such as, for example, bottles, drinking ampoules or portion packs for oral or rectal administration. The active compound remains suspended for a storage time of any desired length, without sedimenting irreversibly and without forming lumps or precipitating on the walls of the vessel.

The medical field of application of the sucralfate suspensions according to the invention is completely analogous to that for the known administration forms containing sucralfate as the active compound, in particular protection and healing of mucous membranes which have been attacked in the digestive tract in humans, in particular relief of symptoms and healing in cases of gastric and duodenal ulcers. However, the agent can also be advantageously used in veterinary medicine for combating emesis and/or diarrhoea. For corresponding treatments, the suspension is usually administered orally in a dosage analogous to the known administration forms of sucralfate. If appropriate, however, such suspensions can also be administered rectally. This is a particular advantage of the sucralfate suspensions according to the invention, since this type of use was virtually impossible with the previously known forms of administration.

EXAMPLE 1

5 ml of an oral suspension with 20% by weight of sucralfate contain

| | |
|---|---|
| sucralfate | 1.118 g |
| NaH$_2$PO$_4$ | 0.03 g |
| xanthan gum | 0.02 g |
| glycerol | 0.50 g |
| sodium methyl-4-hydroxybenzoate | 0.0025 g |
| sodium propyl-4-hydroxybenzoate | 0.0025 g |
| aromatic substances | q.s. |
| water | to 5 ml |

EXAMPLE 2

100 ml of a rectal suspension with 10% by weight of sucralfate contain

| | |
|---|---|
| sucralfate | 11.18 g |
| NaH$_2$PO$_4$ | 0.40 g |
| xanthan gum | 0.19 g |
| glycerol | 10.00 g |
| sodium methyl-4-hydroxybenzoate | 0.05 g |
| sodium propyl-4-hydroxybenzoate | 0.05 g |
| water | to 100 ml |

EXAMPLE 3

5 ml of an oral suspension with 19% by weight of sucralfate contain

| | |
|---|---|
| sucralfate | 1.099 g |
| NaH$_2$PO$_4$.2H$_2$O | 0.025 g |

| -continued | |
|---|---|
| xanthan gum | 0.025 g |
| glycerol | 1.000 g |
| sodium methyl-4-hydroxybenzoate | 0.00375 g |
| sodium propyl-4-hydroxybenzoate | 0.002 g |
| saccharin-Na | 0.0003 g |
| aromatic substances | 0.0019 g |
| water | to 5 ml (=5.775 g) |

We claim:

1. Pharmaceutical formulations in the form of suspensions containing sucralfate, characterised in that they contain, based on the sucralfate, 1-5% by weight of xanthan gum and 1-12.5% by weight of at least one peptiser.

2. Pharmaceutical formulations according to claim 1, characterised in that the peptiser is at least one salt of phosphoric acid or citric acid.

3. Pharmaceutical formulations according to claim 1 or 2, characterised in that they contain 1-40% by weight of sucralfate, based on the total amount.

4. Method of stabilising pharmaceutical formulations in the form of suspensions containing sucralfate, characterised in that 1-5% by weight of xanthan gum and 1-12.5% by weight of at least one peptiser, based on the content of sucralfate, are added to these formulations.

* * * * *

UNITED STATES PATENT AND TRADEMARK OFFICE
CERTIFICATE OF CORRECTION

PATENT NO. : 4,885,281

DATED : December 5, 1989

INVENTOR(S) : ULLRICH HANSTEIN ET AL

It is certified that error appears in the above-identified patent and that said Letters Patent is hereby corrected as shown below:

Title page, Foreign Application Priority Data:

reads "Aug. 22, 1984 [DE] Fed. Rep. of Germany.......3430807"

should read --Aug. 22, 1984 [DE] Fed. Rep. of Germany.......3430809--

Signed and Sealed this

Fifteenth Day of January, 1991

Attest:

HARRY F. MANBECK, JR.

*Attesting Officer*      *Commissioner of Patents and Trademarks*